United States Patent [19]
Sharp et al.

[11] Patent Number: 5,941,702
[45] Date of Patent: Aug. 24, 1999

[54] AIR-ABRADING TOOL

[75] Inventors: Michael C. Sharp, Centerport; Kevin Klocek, Roslyn Heights, both of N.Y.

[73] Assignee: Parkell Products, Inc., Farmingdale, N.Y.

[21] Appl. No.: 09/018,079

[22] Filed: Feb. 3, 1998

[51] Int. Cl.[6] .................................................. A61C 3/02
[52] U.S. Cl. .............................................. 433/88; 433/80
[58] Field of Search ................................... 433/88, 80, 86

[56] References Cited

U.S. PATENT DOCUMENTS

| | | | |
|---|---|---|---|
| 1,398,527 | 11/1921 | Muspratt | 433/88 |
| 2,661,537 | 12/1953 | Angell | 433/88 |
| 4,540,365 | 9/1985 | Nelson et al. | 433/88 |
| 4,648,840 | 3/1987 | Conger, Sr. | 433/125 |
| 4,776,794 | 10/1988 | Meller | 433/88 |
| 4,941,298 | 7/1990 | Fernwood et al. | 433/88 |
| 4,950,160 | 8/1990 | Karst | 433/88 |
| 5,199,229 | 4/1993 | Herold et al. | 433/88 |
| 5,234,338 | 8/1993 | Young | 433/80 |
| 5,501,596 | 3/1996 | Bailey | 433/86 |

*Primary Examiner*—John J. Wilson
*Attorney, Agent, or Firm*—Hoffmann & Baron, LLP

[57] ABSTRACT

A handpiece for a dental instrument includes a solid body having internally reamed passageways through which a fluid is carried. The handpiece may be a dental air-abrading tool for etching hard surfaces to enhance bond strength of adhesives, which includes a solid body having internally reamed passageways through which a gaseous fluid and an abrasive material are carried. A connector is mounted on one end of the body for connecting one of the body's internal passageways to a supply of gaseous fluid and a nozzle is mounted on the other end of the body for directing the gaseous fluid to a surface. A supply of an abrasive material is coupled to another internal passageways of the body. The nozzle includes an internal mixing chamber for mixing the gaseous fluid and abrasive material entering therein from the body's internal passageways. A switch is mounted on the body for activating the flow of gaseous fluid and abrasive material through the body. The switch includes a valve which is slidably mounted within a gaseous fluid passageway between a first position and a second position such that in its first position the valve blocks the flow of gaseous fluid and in its second position the valve allows the gaseous fluid to flow through the body. The switch also includes a trigger pivotally mounted on the body to move the valve alternatively between its two positions. The components of the handpiece are all made from high temperature materials allowing the entire handpiece to be sterilized by autoclaving.

14 Claims, 6 Drawing Sheets

AIR-ABRADING TOOL

BACKGROUND OF THE INVENTION

1. Field of the Invention

The present invention relates generally to a handpiece for a dental instrument and more specifically to a dental air-abrading tool used for etching or roughening hard dental surfaces such as metals, porcelains or composites, to increase the surface area to which adhesive composites are applied and thereby to dramatically improve bond strength.

2. Description of the Prior Art

Use of small etching tools that are hand operated is well known in the dental industry where preparation of artificial dental substrates is often required for repair and cementing procedures. Such tools operate by directing a gaseous stream mixed with an abrasive material to the surface to be prepared. The gaseous medium, (often compressed air), and small solid particles comprising the abrasive material are supplied to the tool and are mixed so that the abrasive material becomes entrained within the gaseous medium. The mixture is then discharged through a nozzle upon activation of the tool by the operator. Numerous types of these instruments are available on the market and are generally in the form of a hand-held device with various combinations of internal components.

For example, U.S. Pat. No. 4,941,298 to Fernwood et al., discloses an apparatus for abrading surfaces through mechanical sandblasting principles using a jet stream containing a mixture of solid particles and compressed air. The apparatus comprises a hollow tubular handle with a nozzle at one end for dispensing the mixture and a member at the other end for receiving the compressed air and solid particles. Within the hollow tubular handle are flexible tubes which individually carry the compressed air and the solid particles to a mixing chamber located within the nozzle. A pinch lever is also provided to inhibit the compressed air flow by compressing the air supply tube in the stand-by mode of the tool. The tool is activated by depressing a button which releases the pinch lever and allows the supply tube to return to its original shape thereby releasing the blockage of the air supply. When the button is released, the pinch lever returns to its original position and compresses the air supply tube again. This type of activating button has the disadvantage that when the button is pushed, the tip of the device tends to jerk a bit. As a result, the operator may spray abrasive where it is not desired.

U.S. Pat. No. 4,648,840 to Conger, Sr., discloses a dental polisher having a pair of conduits concentrically arranged within the polisher's body for providing flows of abrasive material and fluid. The conduits extend into a nozzle for discharging and directing the flow to a surface. Other conventional devices are shown in U.S. Pat. No. 4,776,794 to Meller, U.S. Pat. No. 5,199,229 to Herold et al., and U.S. Pat. No. 4,950,160 to Karst, each disclosing similar instruments comprising combinations of internal tubes, pipes, conduits, etc.

A common drawback to the above mentioned instruments is that in most instances the combination of flexible tubes, pipes and other internal components are difficult to install within the instrument resulting in high costs of manufacture. Also, with instruments operated by the constant compressing and releasing of flexible tubing the problem of deterioration of the tubing and eventual leakage arises. These type of instruments are prone to clogging and are often difficult to clean. Since the internal flexible tubes are not necessarily made of high temperature materials, it may not be possible to sterilize the body of the instrument using a standard autoclave. Sterilizing just the nozzle of conventional devices may not be enough to prevent cross-infection. Accordingly, it would be advantageous to provide a handpiece for a dental instrument which is easy to manufacture, reliable in operation, easy to clean and fully sterilizable by autoclaving.

OBJECTS AND SUMMARY OF THE INVENTION

It is an object of the present invention to provide a low cost, easily manufactured handpiece for a dental instrument which has internal bores or passageways formed within the handpiece as opposed to flexible tubing and other related internal components.

It is another object of the present invention to provide a handpiece for a dental instrument having a solid body which is sterilizable by standard autoclaving techniques.

It is yet a further object of the present invention to provide a dental air-abrading tool encompassing the above objects and which includes a trigger mechanism for controlled release of abrasive material and which provides ease of use for both right-handed and left-handed operators.

It is yet a further object of the present invention to provide a dental air-abrading tool which includes a nozzle which can rotate 360 degrees to perform any desired dental procedure.

The present invention is a low-cost, reliable handpiece for a dental instrument which alleviates the above-mentioned drawbacks. Generally, the handpiece includes a solid body made from a high temperature material and having internally formed bores or passageways for permitting fluid flow through the body. Since the body is made from a high temperature material, it is fully sterilizable by autoclaving. Attachable to the body may be a nozzle for directing the fluid to a surface and a switch for activating the flow of fluid through the handpiece.

The handpiece may be in the form of a dental air-abrading tool which includes a solid body as described above and also includes a connector to a supply of a gaseous fluid, a supply of an abrasive material, a nozzle for mixing and discharging the abrasive material and gaseous fluid and a switch for activating the tool.

The tool is provided with a connector mounted on a proximal end of the body for coupling the tool to a supply of a gaseous fluid. A fluid connection comprising a first axial bore, a first radial bore and a second axial bore, extending from the proximal end of the body to a distal end, is formed within the body as a means for supplying a gaseous fluid to a nozzle fixed at the distal end. A second fluid connection comprising a second radial bore and a third axial bore, extending from the second radial bore to the distal end of the body, is also formed within the body as a means for supplying the abrasive material to the nozzle.

The abrasive material is contained in a canister which is removably attached to the second radial bore. The canister may be provided with a tube having a first end generally disposed within the canister and a second end having a cooperating coupling device for coupling the canister to the second radial bore.

The nozzle fixed at the distal end of the tool has an internal mixing chamber for mixing the gaseous fluid entering therein from the second axial bore and the abrasive material entering therein from the third axial bore. The nozzle is also provided with a movable tip for directing the mixture to a surface.

The tool is provided with a switch which may be internally activated at the first radial bore or may be activated from an external source (i.e., a footpedal). The internal switch generally comprises a valve slidably mounted within the first radial bore and a pivotally mounted trigger which moves the valve longitudinally within the first radial bore between a first position and a second position. When the valve is in the first position, it blocks the first axial bore relative to the second axial bore thereby prohibiting flow of the gaseous fluid through the tool. When the valve is in the second position, the blockage is removed and the fluid may flow from the first axial bore to the second axial bore and then into the internal mixing chamber of the nozzle.

The moving fluid stream passing through the internal mixing chamber of the nozzle generates a vacuum in the third axial bore. This causes a suction which pulls the abrasive material up through the tube of the canister, through the third axial bore of the body and into the mixing chamber of the nozzle where it becomes entrained in the gaseous fluid. This mixture is then discharged to a surface through the nozzle tip.

As a result, the present invention provides a handpiece for a dental instrument which is simple and inexpensive to manufacture, yet less prone to failure than conventional apparatus. The lack of flexible tubing or conduits in the present invention also minimizes the possibility of leakage and clogging. Finally, the relatively few components of the present invention, and the ease with which they are disassembled, enhance the ability to easily clean the handpiece for subsequent uses. A handpiece construction of high temperature materials permits it to be fully autoclaved for sterilization.

A preferred form of the handpiece, as well as other embodiments, objects, features and advantages of this invention, will be apparent from the following detailed description of illustrative embodiments thereof, which is to be read in connection with the accompanying drawings.

DETAILED DESCRIPTION OF THE PREFERRED EMBODIMENTS

While the invention relates generally to a handpiece for a dental instrument, in a preferred embodiment the present invention is a dental air-abrading tool designed to enhance the bond strength of composite resins to a variety of substrates encountered in dentistry, e.g., cast alloys, porcelains and composite resins. It is known in the art that adhesives bond much better to these materials when the surface of the substrate has been roughened by air-abrasion. This device is not intended for nor recommended for tooth preparation, caries removal, or removal of amalgam restorations.

Referring to the drawings, a preferred embodiment of an air-abrading tool 10 formed in accordance with the present invention is shown. Generally, the air-abrading tool comprises an elongated solid body 11, a fluid supply connector 26, a supply of an abrasive material 29, a nozzle 35 and a switch 43.

Figure 1:
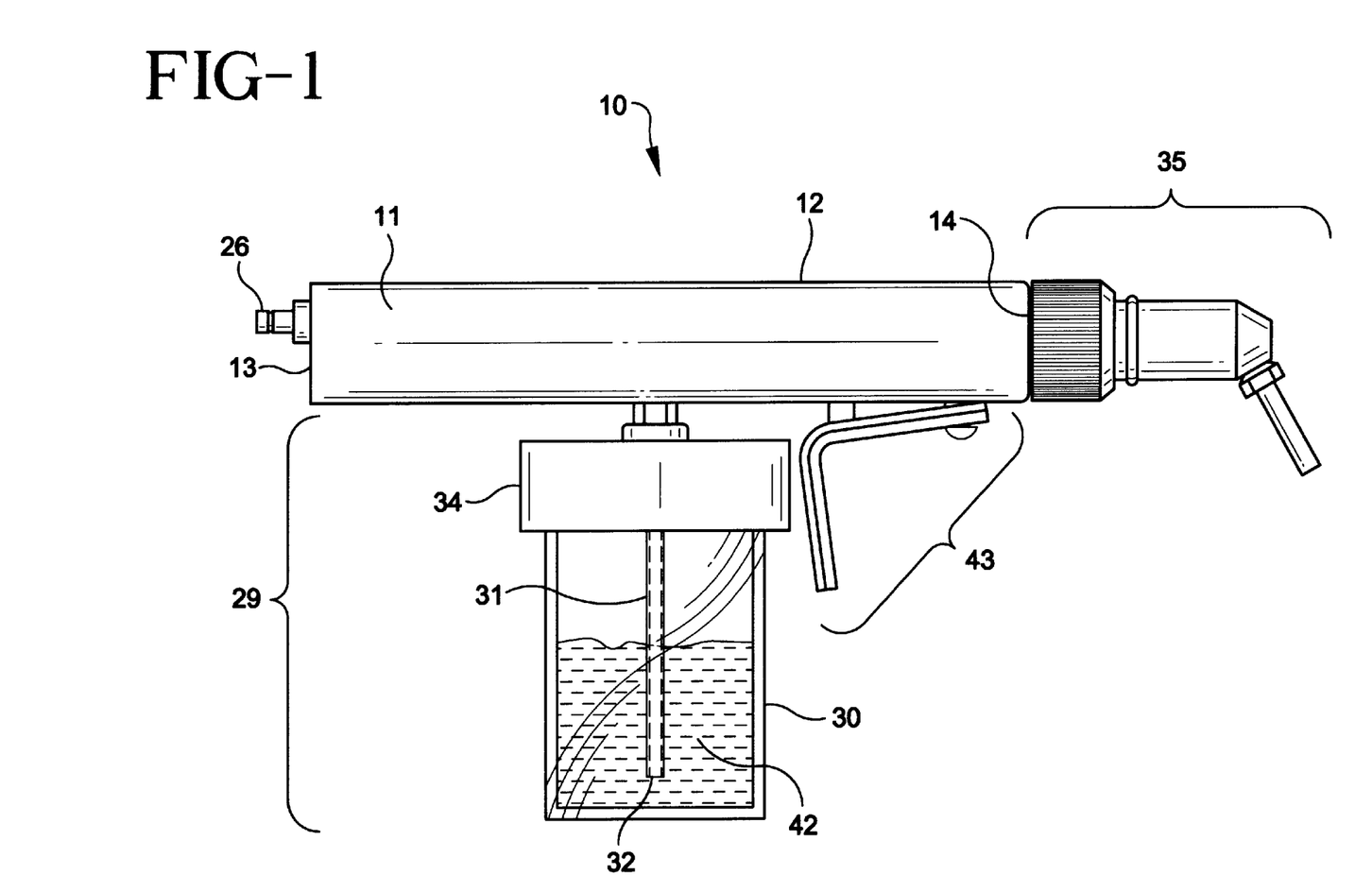
FIG. 1 is a side view of the assembled air-abrading tool.
Figure 2:
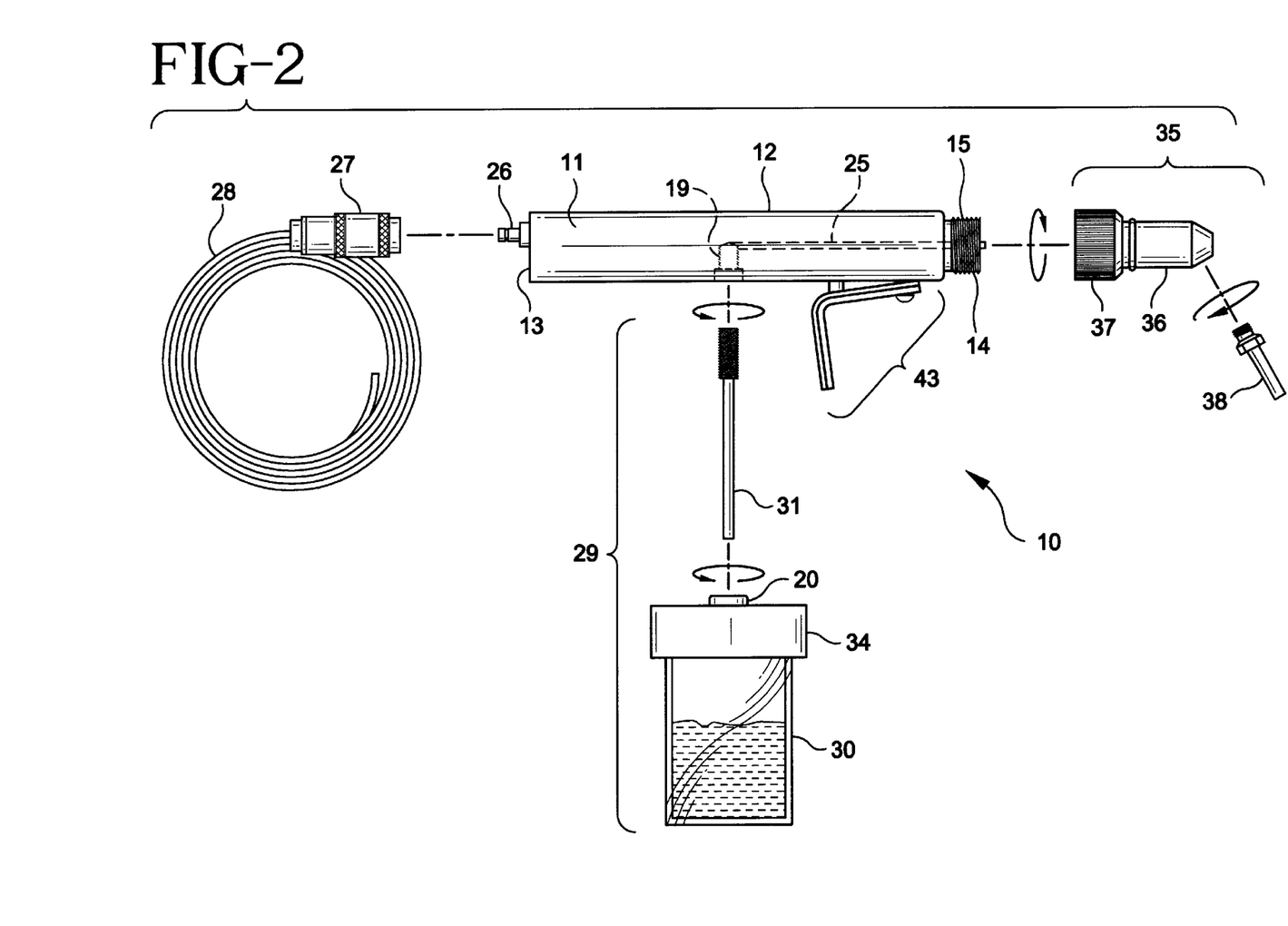
FIG. 2 is a partially exploded side view of the air-abrading tool.
Figure 3:
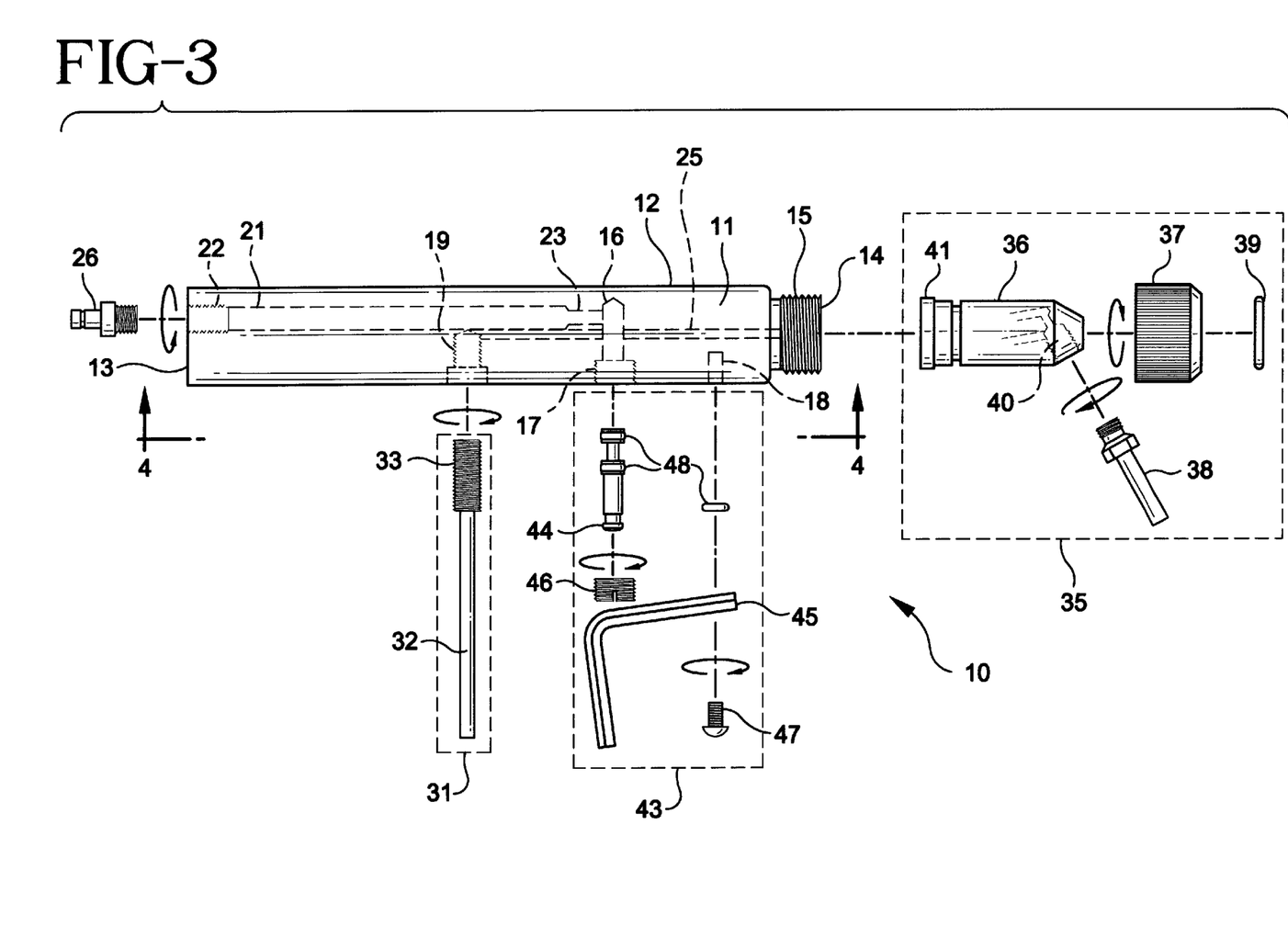
FIG. 3 is a fully exploded side view of the air-abrading tool.
Figure 4:
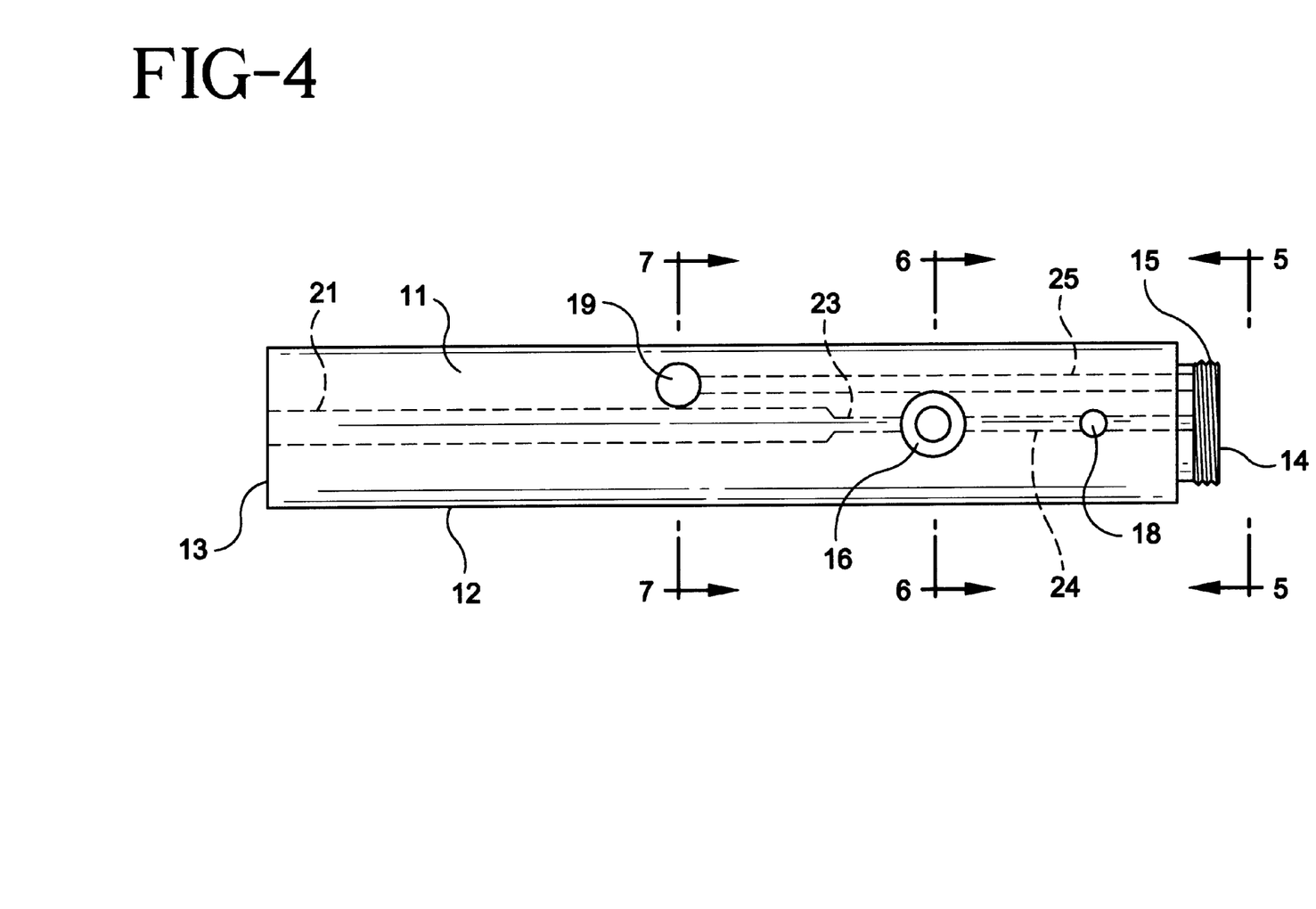
FIG. 4 is a bottom view of the solid body of the air-abrading tool.
Figure 5:
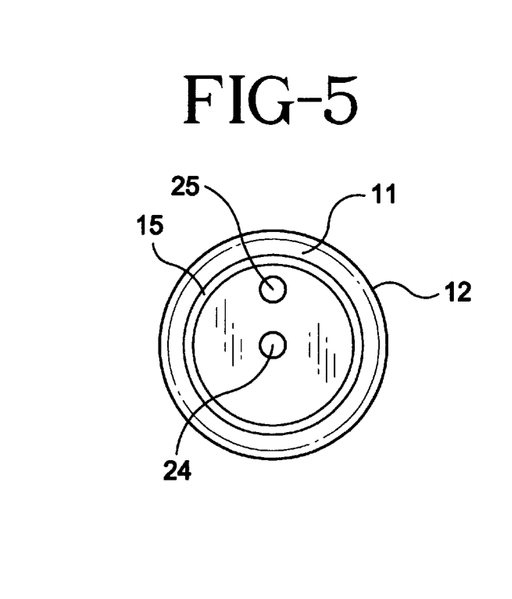
FIG. 5 is a front view of the solid body of the air-abrading tool.
Figure 6:
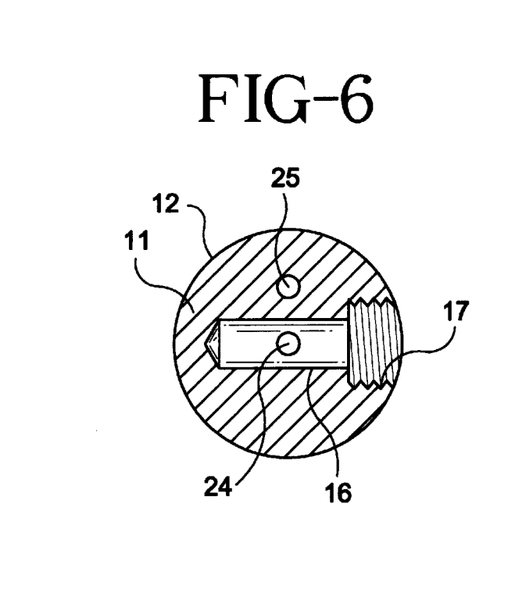
FIG. 6 is a cross-sectional view of the solid body of the air-abrading tool taken at the first radial bore.
Figure 7:
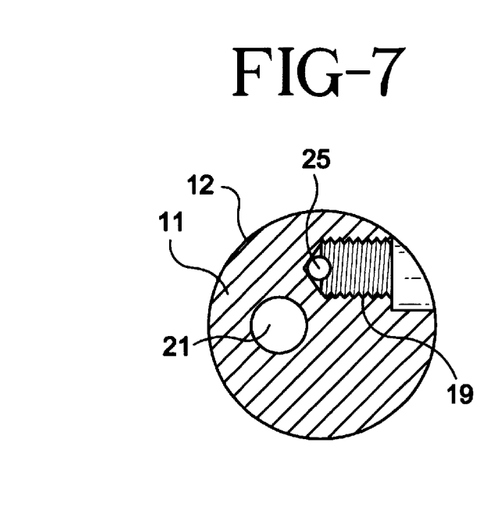
FIG. 7 is a cross-sectional view of the solid body of the air-abrading tool taken at the second radial bore.

In the preferred embodiment, the solid body 11 has an outer surface 12, a proximal end 13, a distal end 14 and may be generally cylindrical in shape. The body may be made from any suitable rigid material. Disposed on the distal end of the body are means to connect the body to a nozzle 35. As shown in FIGS. 2, 3 and 4, the means may comprise a threaded connection 15 formed on the distal end of the body or, alternatively, any known connection mechanism may be used. The body 11 further comprises a plurality of internal bores. These bores may be formed using conventional machining techniques known in the art (e.g., drilling, reaming, electric discharge machining, etc.).

A first radial bore 16 is disposed substantially perpendicularly to the outer surface of the body and is positioned between the proximal and distal ends. The depth of this bore is not critical but, as will be discussed shortly, it is important that the first radial bore extend deep enough into the body so as to be in fluid communication with a first and second axial bore. The diameter of the first radial bore must be sufficiently precise so as to enable close but slidable contact with a valve 44 fitted with O-rings 48. The first radial bore should also be provided with threaded connection means 17 for engaging a mating valve retainer 46. Located near the first radial bore is another internal thread 18 for connecting a trigger 45 to the body. (The valve, O-rings, retainer and trigger will be discussed in detail below.) A second radial bore 19 is disposed perpendicularly to the outer surface of the body and is positioned between the proximal and distal ends. This bore may be formed by simply threading a hole to a depth sufficient enough so as to be in fluid communication with a third axial bore to be discussed shortly.

Extending longitudinally within the body are three axial bores 21, 24 and 25. The first axial bore 21 extends from the proximal end of the body and terminates at the first radial bore 16. The second axial bore 24 (see FIG. 4) extends from the distal end of the body and terminates at the first radial bore from the opposite direction. Thus, the first axial bore 21, the second axial bore 24 and the first radial bore are in fluid communication. The third axial bore 25 extends from the distal end of the body and terminates at the second radial bore so as to be in fluid communication therewith. The first axial bore 21 is also provided with an internal thread 22 at the proximal end for engaging a connector 26. The first axial bore 21 may also be provided with a decreased diameter 23 opposite the proximal end of the body to enhance fluid communication with the first radial bore 16.

Fitted into the internal thread 22 of the first axial bore 21 is a connector 26 which connects to a mating connector 27 of a supply line 28 of a gaseous fluid (e.g. compressed air). Compressed air can be supplied to the tool at air pressures between 40 and 100 psi, but best results are generally obtained at 80–90 psi. Connectors 26 and 27 may be mating male/female quick-disconnect fittings which are commonly known in the art.

The air-abrading tool 10 is also provided with its own self-contained supply 29 of an abrasive material. The supply comprises a pickup tube 31, a canister 30, a canister cap 34 and an abrasive material 42 contained within the canister.

The abrasive material is preferably 50 micron aluminum oxide but may be any small particulate material known in the art to be suitable for air-abrading purposes. The canister cap 34 should be suitably secured over the top of the canister so as to seal the abrasive material therein. A threaded connection 20 is provided through the canister cap for access to the abrasive material by the pickup tube 31. The pickup tube 31 has a first end 32 and an externally threaded second end 33 which mates with both the second radial bore 19 of the body 11 and the threaded connection 20 of the canister cap 34. The pickup tube 31 is inserted through the canister cap 34 so that the first end 32 of the tube is generally disposed within the abrasive material 42. The externally threaded second end 33 is then coupled to the threaded connection 20 of the canister cap 34 leaving a portion of the threaded second end of the pickup tube extending out of the canister. The exposed portion of the threaded second end is then coupled to the second radial bore 19 so that the supply 29 of abrasive material is secured to the body 11 and fluid connection is made between the interior of the canister 30 and the third axial bore 25.

Figure 9:
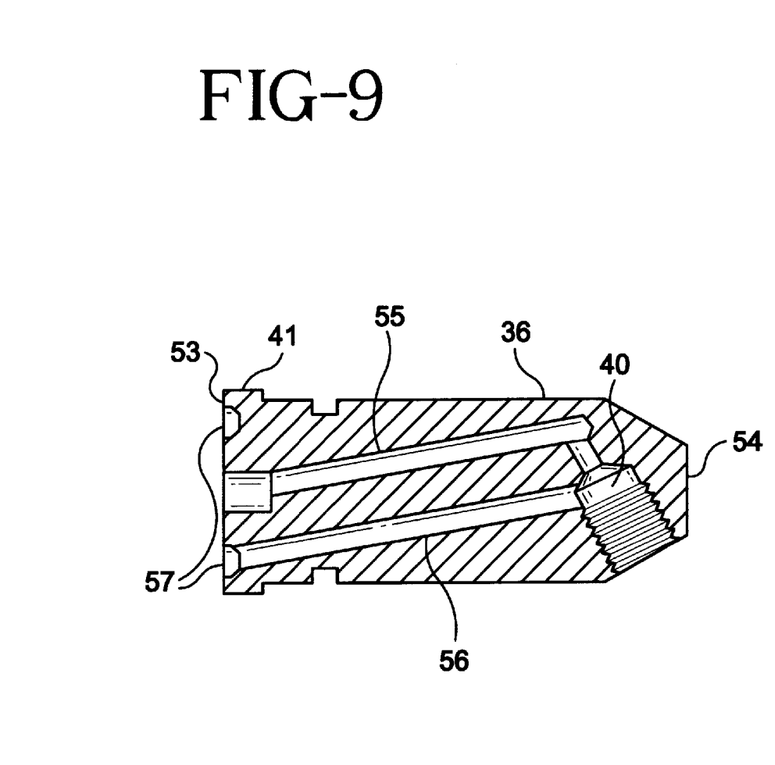
FIG. 9 is a cross-sectional view of the nozzle head of the air-abrading tool.

Disposed on the distal end 14 of the body is a nozzle 35 for directing the abrasive material to a surface. The nozzle comprises a nozzle head 36, a knurled nut 37, a nozzle tip 38 and a retaining ring 39. The nozzle head may be made from the same or different material as the body. The nozzle head 36 is generally cylindrical in shape having an inlet end 53 and a discharge end 54. (See FIG. 9). Formed within the nozzle head is a gaseous fluid inlet bore 55, an abrasive material inlet bore 56 and an internal mixing chamber 40. The gaseous fluid inlet bore 55 and the abrasive material inlet bore 56 extend from the inlet end 53 of the nozzle head and terminate at the internal mixing chamber 40 at the discharge end 54 to be in fluid communication. Also formed on the inlet end 53 of the nozzle head is a circular groove 57 to be in fluid communication with the abrasive material inlet bore 56. The gaseous fluid inlet bore 55 is positioned at the inlet end 53 of the nozzle head to be in fluid communication with the second axial bore 24 of the body 11 when the nozzle head is assembled to the body. Similarly, the abrasive material inlet bore 56 and the circular groove 57 are positioned to be in fluid communication with the third axial bore 25 of the body upon assembly. The circular groove 57 maintains fluid connection between the body and the nozzle head allowing full 360 degree rotation of the nozzle head. Thus, during operation of the tool, gaseous fluid from the second axial bore 24 of the body 11 flows through the gaseous fluid inlet bore 55 of the nozzle head and enters the internal mixing chamber 40 where it is mixed with abrasive material entering therein from the third axial bore 25 of the body through the abrasive material inlet bore 56 of the nozzle head.

The nozzle 35 is fastened to the distal end 14 of the body by means of an internally threaded knurled nut 37. The retaining ring 39 is first positioned and secured over the nozzle head 36 in proximity to a shoulder 41 of the nozzle head. The retaining ring 39 helps to keep the knurled nut 37 from detaching from the nozzle head 36 when disassembled. The knurled nut 37 retains the shoulder 41 and the retaining ring 39 and engages the external thread 15 of the body to securely fasten the nozzle head to the body. O-rings (not shown) may be provided at the nozzle head-body interface to prevent leakage. Finally, a nozzle tip 38, preferably made from a suitable wear resistant or surface treated material (e.g., tungsten carbide), is removably fastened to the nozzle head 36 by means of a threaded connection.

Figure 8:
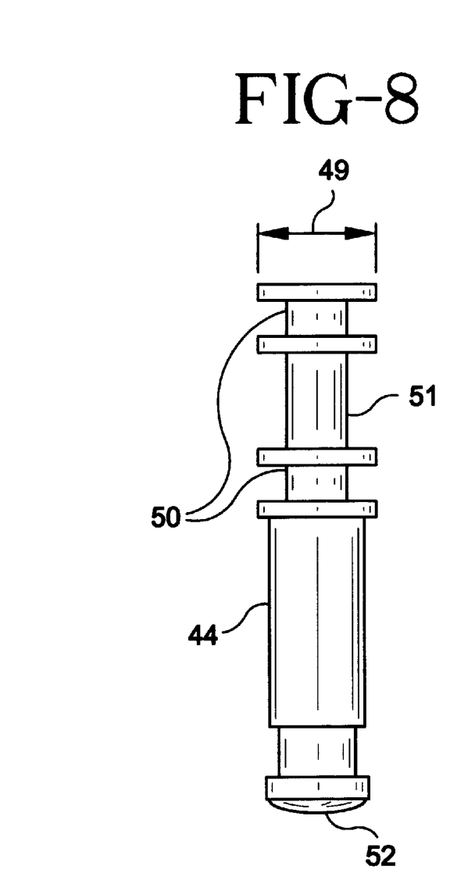
FIG. 8 is a side view of the valve of the air-abrading tool.

In a preferred embodiment, the tool is activated by a switch 43 disposed at the first radial bore 16. External sources, such as a footpedal, may also be used to activate the tool. The switch comprises a valve 44, a trigger 45, a valve retainer 46, O-rings 48 and a trigger mounting screw 47. The valve 44, trigger 45, valve retainer 46 and trigger mounting screw 47 are preferably made from stainless steel to minimize corrosion. Referring to FIG. 8, the valve 44 is generally cylindrical in shape having a maximum diameter 49 substantially equal to the diameter of the first radial bore 16 so as to enable close but slidable contact between the valve 44 and the first radial bore. The valve 44 is also provided with two annular grooves 50, a channel 51 and a spherical end 52. The channel 51 is formed on the valve between the annular grooves 50 opposite the spherical end 52. 0-rings 48 are fitted in the annular grooves 50 of the valve to prevent leakage of the gaseous fluid as it passes from first axial bore 21 to second axial bore 24. The valve 44 is slidably mounted within the first radial bore 16 and is retained therein by valve retainer 46 and trigger 45. The valve retainer 46 may be mounted within the first radial bore by threaded connection means 17. The valve retainer 46 retains the valve 44 within the first radial bore 16 but allows the valve to move longitudinally within the bore between a first position and a second position. The spherical end 52 of the valve protrudes through the valve retainer 46 to engage the trigger 45.

The trigger 45 is generally L-shaped with a hole at one end for mounting to the body 11. The trigger 45 is connected to the body by trigger mounting screw 47 which engages internal thread 18 of the body. An additional O-ring 48 may be provided between the trigger and the body to enhance pivoting of the trigger. In mounting the trigger 45 to the body, the trigger must engage the spherical end 52 of the valve 44 protruding through the valve retainer 46. When the tool is connected to a supply of gaseous fluid, the pressure of the fluid from the first axial bore 21 forces the valve 44 downward into its first or standby position. When the valve 44 is in its first or standby position, the O-rings 48 block the flow of gaseous fluid between the first axial bore 21 and the second axial bore 24. To activate the flow of gaseous fluid, the operator of the tool simply depresses and holds the trigger 45, thus forcing the valve upward to its second position. In this second position, the valve 44 is positioned so as to allow the gaseous fluid to flow from the first axial bore 21, past the valve channel 51, to the second axial bore 24. When the trigger is released, the pressure of the fluid again forces the valve downward into its first position stopping the flow of the gaseous fluid. This pistol-type trigger allows gentle squeezing to activate the tool. As a result, the nozzle tip remains pointed at the target without any sudden movement as associated with conventional push-button devices. Also, unlike some button switches, the trigger is equally accessible to both right-handed and left-handed operators.

When the tool is activated, gaseous fluid entering the first axial bore 21 flows into the second axial bore 24 through the first radial bore 16. From the second axial bore the fluid flows through the gaseous fluid inlet bore 55 into the internal mixing chamber 40 of the nozzle head 36 and out through the nozzle tip 38. The moving fluid stream passing through the internal mixing chamber generates a vacuum in the third axial bore 25 and, in turn, the pickup tube 31. This causes a suction which pulls abrasive material 42 from the canister 30 up through the pickup tube 31, through the third axial bore 25 and the abrasive material inlet bore 56, and into the internal mixing chamber 40 where it becomes entrained in the fast moving fluid stream. The gaseous fluid/abrasive material mixture is then discharged through the nozzle tip 38 to a surface to be prepared.

If the air-abrading tool is used intra-orally, a rubber dam, nasal and eye protection for the patient, as well as high volume evacuation must be used. It is recommended that the operator wear safety glasses and a mask. The air-abrading tool may also be used extra-orally.

When used intra-orally, the specific area to be air-abraded is isolated and adjacent areas not to be treated by abrasion should be protected. The nozzle tip of the air-abrading tool should be placed approximately 2–3 mm to the surface to be abraded with the high volume evacuator immediately adjacent to the area. After activating the tool with the trigger, the nozzle tip is moved across the surface to be abraded with a smooth, sweeping motion. About 2 or 3 seconds of air-abrasion is all that is required to produce a proper dull, matte-like finish of the treated surface. Abrasive material which may have collected in the rubber dam is then rinsed and evacuated from the patient's mouth and adhesive may then be applied to the treated surface.

Since the air-abrading tool of the present invention comprises no internal flexible tubing which may degrade under high temperatures, the entire body of the tool, along with the nozzle, may be sterilized using standard autoclaving techniques. To autoclave the entire device, it must first be back-flushed. This is accomplished by first removing the abrasive material canister and cap. The operator's finger is placed over the nozzle tip and the tool is briefly activated (about 1 second) to blow out residual abrasive material from the pickup tube. The pickup tube should be placed over a waste receptacle to capture expelled material during this procedure. The air-abrading tool should then be removed from the air supply line and thoroughly washed. The entire tool can then be placed into an autoclave for at least 20 minutes at 250 degrees F. and 15 psi. If necessary, the tool can also be easily disassembled for cleaning and servicing. Before subsequent use, the tool should again be back-flushed (as described above) to remove any residual moisture from the internal passages. The tool should be fully dry before subsequent use.

Although the illustrative embodiments of the present invention have been described herein with reference to the accompanying drawings, it is to be understood that the invention is not limited to those precise embodiments, and that various other changes and modifications may be effected therein by one skilled in the art without departing from the scope or spirit of the invention, and it is intended to claim all such changes and modifications as fall within the scope of the invention.

We claim:

1. A handpiece for a dental instrument comprising: an elongated solid body made from a high temperature material, said handpiece body forming a handle for being grasped by a user and having a plurality of substantially parallel longitudinal passageways bored through said solid body, said passageways forming a fluid flow conduit extending from a first end of said body connectable to a supply of fluid to a second end of said body for discharge therefrom, and wherein said handpiece is sterilizable by autoclaving.

2. The handpiece defined in claim 1, wherein said handpiece further comprises a nozzle attachable to said second end of said body for directing said material to a surface.

3. The handpiece as defined in claim 1, wherein said handpiece further comprises a switch for activating the flow of said fluid.

4. The handpiece as defined in claim 2, wherein said handpiece further comprises a switch for activating the flow of said fluid.

5. An air-abrading tool for etching hard surfaces to enhance bond strength of adhesives which comprises: a handpiece in the form of an elongated solid body forming a handle for being grasped by a user and having an outer surface, a proximal end, a distal end, a plurality of substantially parallel longitudinal passageways bored through said solid body, said passageways forming a fluid flow conduit extending from said proximal end to said distal end, and a first connector for connecting said handpiece body proximal end to a supply of a gaseous fluid and a second connector for connecting said handpiece body to a supply of an abrasive material; a nozzle attachable to said distal end of said handpiece body, said nozzle having a discharge orifice for directing said abrasive material and said gaseous fluid to a surface to be abraded; and a switch for activating a flow of said gaseous fluid through said handpiece.

6. The air-abrading tool defined in claim 5, wherein said air-abrading tool is made from a high temperature material and is thereby sterilizable by autoclaving.

7. The air-abrading tool defined in claim 5, wherein said solid body comprises, a first radial bore extending perpendicularly to said body outer surface and positioned between said proximal end and said distal end, a second radial bore extending perpendicularly to said body outer surface and positioned between said proximal end and said distal end for coupling said supply of an abrasive material thereto, a first axial bore formed within said body extending from said proximal end and terminating at said first radial bore to be in fluid communication therewith, a second axial bore formed within said body extending from said distal end and terminating at said first radial bore to be in fluid communication therewith, a third axial bore formed within said body extending from said distal end and terminating at said second radial bore to be in fluid communication therewith, and a connector mounted on said proximal end for connecting said first axial bore to a supply of a gaseous fluid, and wherein said nozzle includes an internal chamber for mixing the gaseous fluid entering therein from said second axial bore and the abrasive material entering therein from said third axial bore, and wherein said switch is coupled to said first radial bore.

8. The air-abrading tool defined in claim 7, wherein said switch comprises a valve and a trigger, said valve being slidably mounted within said first radial bore between a first position and a second position such that when said valve is in said first position said valve blocks said first axial bore relative to said second axial bore, and when said valve is in said second position gaseous fluid may flow from said first axial bore to said second axial bore and wherein said trigger is pivotally mounted on said outer surface of said body to move said valve alternatively from said first position to said second position.

9. The air-abrading tool defined in claim 8, wherein said supply of abrasive material to said body comprises a tube and a canister, wherein said tube has a first end and a second end, said first end being generally disposed within said canister and said second end having a cooperating coupling device for coupling said canister to said second radial bore.

10. The air-abrading tool defined in claim 7, wherein said supply of abrasive material to said body comprises a tube and a canister, wherein said tube has a first end and a second end, said first end being generally disposed within said canister and said second end having a cooperating coupling device for coupling said canister to said second radial bore.

11. The tool as set forth in claim 7, wherein said connector comprises a quick connect fitting for attachment to a mating quick connect coupling of the supply of gaseous fluid.

12. An air-abrading tool, for etching hard surfaces to enhance bond strength of adhesives, which comprises:

an elongated solid body having an outer surface, a proximal end and a distal end, said body further comprising,
- a first radial bore extending perpendicularly to said body outer surface and positioned between said proximal end and said distal end,
- a second radial bore extending perpendicularly to said body outer surface and positioned between said proximal end and said distal end for coupling a supply of an abrasive material thereto,
- a first axial bore formed within said body extending from said proximal end and terminating at said first radial bore to be in fluid communication therewith,
- a second axial bore formed within said body extending from said distal end and terminating at said first radial bore to be in fluid communication therewith,
- a third axial bore formed within said body extending from said distal end and terminating at said second radial bore to be in fluid communication therewith;

a connector mounted on said proximal end for connecting said first axial bore to a supply of a gaseous fluid;

a nozzle disposed on said distal end for directing the abrasive material to a surface, said nozzle including an internal chamber for mixing the gaseous fluid entering therein from said second axial bore and the abrasive material entering therein from said third axial bore; and a switch coupled to said first radial bore for activating the flow of gaseous fluid and abrasive material through said body.

13. A handpiece for a dental instrument which comprises:

an elongated solid body made from a high temperature, autoclavable material and having a plurality of internally formed substantially parallel longitudinal passageways extending from a proximal end of said body to a distal end of said body, said passageways permitting fluid flow from said proximal end to said distal end;

a material supply canister having a top and body, said top being connected to said body between said proximal end and said distal end for supplying a material to said flow, said canister being dimensioned to be held in the hand of a user of said handpiece; and a switch connected to said body between said canister and said distal end for activating said fluid flow, said switch being positioned relative to said canister so as to be accessible by the hand holding said canister.

14. The handpiece defined in claim 13, wherein said switch comprises a valve and trigger, said valve being slidably mounted within said body between a first position and a second position such that when said valve is in said first position said valve seals one of said longitudinal passageways, and when said valve is in said second position gaseous fluid may flow from said proximal end to said distal end of said body, and wherein said trigger is pivotally mounted on an outer surface of said body to move said valve alternatively from said first position to said second position.

* * * * *